United States Patent
Mao et al.

(10) Patent No.: US 7,645,909 B2
(45) Date of Patent: Jan. 12, 2010

(54) LINEAR AND BRANCHED ALCOHOL ETHOXYLATES FOR CONTROLLING INSECTS

(75) Inventors: Jianhua Mao, Cincinnati, OH (US); Dean Oester, Cincinnati, OH (US)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 11/830,962

(22) Filed: Jul. 31, 2007

(65) Prior Publication Data

US 2008/0051467 A1 Feb. 28, 2008

Related U.S. Application Data

(60) Provisional application No. 60/822,039, filed on Aug. 10, 2006.

(51) Int. Cl.
*C07C 43/13* (2006.01)

(52) U.S. Cl. .............. 568/622; 568/613; 568/618
(58) Field of Classification Search ............. 568/622, 568/618, 613
See application file for complete search history.

(56) References Cited

U.S. PATENT DOCUMENTS

| | | | | | |
|---|---|---|---|---|---|
| 4,474,678 | A | * | 10/1984 | Lutz et al. | 510/506 |
| 5,141,963 | A | * | 8/1992 | Browning | 514/723 |
| 5,635,194 | A | * | 6/1997 | Dorn et al. | 424/405 |

* cited by examiner

*Primary Examiner*—Elvis O Price

(57) ABSTRACT

Compounds for controlling aquatic breeding insects including an ethoxylated alcohol with a carbon chain length of about 10 to about 24 carbon atoms and about 0 to about 16 moles of ethylene oxide per mole of alcohol, where the carbon chain is linear or branched with an alkyl group are provided. Methods for making branched alcohol ethoxylated compounds and linear secondary alcohol ethoxylated compounds are also provided. Methods for controlling insects with the compounds are also provided.

22 Claims, No Drawings

LINEAR AND BRANCHED ALCOHOL ETHOXYLATES FOR CONTROLLING INSECTS

CROSS-REFERENCE TO RELATED APPLICATIONS

This application claims priority under 35 U.S.C. §119(e) from U.S. Provisional Application No. 60/822,039, filed on Aug. 10, 2006, the entire disclosure of which is hereby incorporated herein by reference.

FIELD OF THE INVENTION

The invention relates generally to insect control agents and methods for controlling the development of insects, and more particularly, to compounds for controlling aquatic breeding insects, method for making the compounds, and methods for controlling the development of insects by treating their breeding sites.

BACKGROUND INFORMATION

Mosquito control is required in many areas of the world. The presence of mosquitoes is not only a nuisance (the biting of humans and other animals), but certain diseases, including, but not limited to, malaria, West Nile virus, certain types of encephalitis, and Dengue Fever, are spread by the mosquito. Many mosquito control agents, including, but not limited to, insecticides or pesticides, however, consist of chemicals toxic to humans and other animals and invertebrates.

Aquatic breeding sites for mosquitoes and other insects include, but are not limited to, salt marshes; ponds; storm water, retention, and detention basins; roadside ditches; grassy swales; fields; pastures; potable water containers; reservoirs; irrigated croplands; woodland pools; tidal waters; sewage and animal waste lagoons; septic ditches; lakes; swamps; and floodwater areas.

Mosquitoes require, as part of their life cycle, standing water in which to develop. The larvae and pupae spend a major part of their life cycle in water. During these aquatic stages of development, mosquitoes are more susceptible to control.

A need remains for insect control agents and methods for controlling the breeding of insects, particularly mosquitoes that are effective over the entire life stage of the insect (larvae, pupae and resting adult) and are biodegradable so that accumulation in the environment is minimal.

SUMMARY OF THE INVENTION

Briefly described, in one aspect of the invention, a compound for controlling aquatic breeding insects includes an ethoxylated alcohol with a carbon chain length of about 10 to about 24 carbon atoms and about 0 to about 16 moles of ethylene oxide per mole of alcohol, where the carbon chain is linear or branched with an alkyl group.

In another aspect of the invention, a compound for controlling aquatic-breeding insects includes an ethoxylated alcohol with about 12 to about 17 carbon atoms, and about 2 to about 4 moles of ethylene oxide per mole of alcohol, where the carbon chain is linear or branched with an alkyl group.

In another aspect of the invention, the compounds described above may be in liquid, encapsulated liquid, gel or granular form. Methods for controlling insects with the compounds described above are also aspects of the invention.

In yet another aspect of the invention, a method for making a branched alcohol ethoxylated compound includes combining an alcohol with about 10 to about 24 carbon atoms and substituted with an alkyl group with a catalyst to form a mixture; reacting ethylene oxide with the mixture to completion; and removing residual ethylene oxide to obtain an ethoxylated branched alcohol with an average of about 2 to about 4 moles of ethylene oxide per mole of alcohol.

According to another aspect of the invention, a method for making a linear secondary alcohol ethoxylated compound includes combining a linear secondary alcohol with about 12 to about 17 carbon atoms with a catalyst to form a mixture; reacting ethylene oxide with the mixture to completion; and removing residual ethylene oxide to obtain an ethoxylated linear secondary alcohol with an average of about 2 to about 4 moles of ethylene oxide per mole of alcohol.

DETAILED DESCRIPTION OF THE INVENTION

Definitions

The terms "a" or "an" as used herein are to describe elements and components of the invention. This is done merely for convenience and to give a general sense of the invention. The description herein should be read to include one or at least one and the singular also includes the plural unless indicated to the contrary.

The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

The term "insects" includes all species of adult mosquitoes and immature mosquitoes (larvae pupae, and emerging adults), in addition to midges and black flies, and the various life stages thereof including chronomid midges, which breed in standing water and require an air/water interface to continue their life cycle.

According to an aspect of the invention, a compound for controlling aquatic breeding insects includes an ethoxylated alcohol with a carbon chain length of about 10 to about 24 carbon atoms and about 0 to about 16 moles of ethylene oxide per mole of alcohol, wherein the carbon chain is linear or branched with an alkyl group. The alcohol may be monosubstituted. The alcohol may be a primary alcohol or a secondary alcohol. The alcohol may have an average carbon chain length of about 12 to about 20 carbon atoms, or an average carbon chain length of about 12 to about 17 carbon atoms. The alcohol may have an average of about 2 to about 8 moles of ethylene oxide per mole of alcohol, or about 2 to about 4 moles of ethylene oxide per mole of alcohol. The compound may be in liquid, encapsulated liquid, gel or granular form. The compound may be water-insoluble and form a film on the surface of a body of water. The aquatic breeding insects include mosquitoes, midges, or black flies. The branched alcohol may contain an alkyl group comprising about 1 to about 5 carbon atoms. The alkyl group may include methyl, ethyl, propyl, isopropyl, butyl, isobutyl, or pentyl.

According to another aspect of the invention, a compound for controlling aquatic-breeding insects includes an ethoxylated alcohol with about 12 to about 17 carbon atoms, and about 2 to about 4 moles of ethylene oxide per mole of alcohol, wherein the carbon chain is linear or branched with an alkyl group. The alkyl group may be mono-substituted on the alcohol, and include about 1 to about 5 carbon atoms. The alkyl group may include methyl, ethyl, propyl, isopropyl, butyl, isobutyl, or pentyl. The compound may be in liquid, encapsulated liquid, gel or granular form. The compound may be water-insoluble and form a film on the surface of a body of water. The aquatic breeding insects include mosquitoes, midges, or black flies. The alcohol may be secondary and the carbon chain may be linear.

According to another aspect of the invention, methods for controlling aquatic breeding insects include treating a body of water with the above-described compounds. The methods include spraying the liquid compound on the body of water, or spreading the granular compound onto the surface of standing water or on the ground prior to the accumulation of standing water. In yet another aspect of the invention, methods for controlling aquatic breeding insects includes applying an effective amount of the compounds described above to a selected surface during the larvae, pupae, or adult life cycles thereof.

According to yet another aspect of the invention, a method for making a branched alcohol ethoxylated compound includes combining an alcohol with about 10 to about 24 carbon atoms and substituted with an alkyl group with a catalyst to form a mixture; reacting ethylene oxide with the mixture to completion; and removing residual ethylene oxide to obtain an ethoxylated branched alcohol with an average of about 2 to about 4 moles of ethylene oxide per mole of alcohol. The alcohol may have an average carbon chain length of about 12 to about 20 carbon atoms, or an average chain length of about 12 to about 17 carbon atoms. The alcohol may be mono-substituted with an alkyl group comprising about 1 to about 5 carbon atoms. The catalyst may be selected from the group consisting of hydrotalcite, NaOH, sodium methylate, and KOH. The step of reacting may be conducted at a temperature of about 150° C. to about 170° C. The reaction may be conducted for a time period of about two hours. The step of removing residual ethylene may include vacuum stripping at a temperature of about 150° C. to about 160° C. for about 30 minutes. The presence of a $C_{16-17}$ alcohol may be predominant, or the presence of a $C_{15}$ alcohol may be predominant.

According to another aspect of the invention, a method for making a linear secondary alcohol ethoxylated compound includes combining a linear secondary alcohol with about 12 to about 17 carbon atoms with a catalyst to form a mixture; reacting ethylene oxide with the mixture to completion; and removing residual ethylene oxide to obtain an ethoxylated linear secondary alcohol with an average of about 2 to about 4 moles of ethylene oxide per mole of alcohol. The catalyst may be selected from the group consisting of hydrotalcite, NaOH, sodium methylate, and KOH. The step of reacting may be conducted at a temperature of about 150° C. to about 170° C. The reaction may be conducted for a time period of about two hours. The step of removing residual ethylene may include vacuum stripping at a temperature of about 150° C. to about 160° C. for about 30 minutes.

Advantageously, applicants have found that the compounds and methods according to an aspect of the invention control the breeding of aquatic insects throughout the entire breeding life cycle.

As described above, the ethoxylated alcohol has an alkyl chain length of about 10 to about 24 carbon atoms and about 0 to about 16 moles of ethylene oxide per mole of alcohol. A suitable alcohol may be linear or branched and substituted with an alkyl group. Branching may occur anywhere along the carbon chain of the alcohol, and is not limited to any particular position.

A suitable alcohol for use in making the ethoxylated alcohol is NEODOL® 67, available from Shell Chemicals in Texas. NEODOL® 67 is a $C_{16}$ and $C_{17}$ high purity mono-branched primary alcohol (according to a recently updated Shell datasheet). Although the primary constituents of NEODOL® 67 comprise $C_{16}$ (31% m/m) and $C_{17}$ (54% m/m) alcohols, a mixture of $C_{14}$-$C_{20}$ alcohols are also present, but in greatly reduced amounts, for example, $C_{14}$ and lower alcohols (<0.5% m/m); $C_{18}$ (7% m/m); and $C_{20}$ (<0.2% m/m). Therefore, when referring to the NEODOL® $C_{16}$ and $C_{17}$ alcohol, it is to be understood that there is present a mixture of alcohols with differing chain lengths, but the presence of a $C_{16}$ and $C_{17}$ alcohol is predominant.

An additional suitable alcohol ethoxylated for use according to an aspect of the invention includes a $C_{15}$ linear secondary alcohol available under the trade name TERGITOL® 15 S 3 from Dow Chemical. TERGITOL® 15 S 3 has an average of about 3 moles of ethylene oxide (EO) per mole of alcohol. Other suitable linear secondary alcohol ethoxylates for use according to an aspect of the invention include those available under the trade name SOFTANOL°, from Shobukai in Japan. For example, SOFTANOL® 30 is a secondary alcohol with an average of about 3 moles EO per mole of alcohol. Suitable SOFTANOL® alcohols also include those having a carbon chain length of about 12 to 14 carbon atoms.

The alcohols are ethoxylated with suitable epoxides, for example, ethylene oxide, and a catalyst. Suitable catalysts include sodium hydroxide, sodium methylate, potassium hydroxide and hydrotalcite. Any type of calcined hydrotalcite catalyst used for the alkoxylation of alcohols may be used in the process according to an aspect of the invention.

In use, the rate of kill is dependent upon the species, the life stage, the habitat and temperature. The compound according to an aspect of the invention is not visible on the surface of the water. To check the habitat for presence and persistence of the product, indicator oil may need to be added. If a tight bead forms on the surface, then the compound is present. Alternatively, the presence of the product may be checked with a galvanized steel wire ring (18-24 G), 0.75-1.5 inches diameter. The ring will float on the surface of untreated water due to the high surface tension, but will sink in water with an effective monomolecular film due to the reduced surface tension of the water. The film will typically persist on the water surface for 5-22 days. Polluted waters will cause more rapid degradation of the film. Mosquitoes and midges that require little or no surface contacts for breathing will be affected by the product during the pupae and emerging adult life stages.

The compound in liquid form is typically applied to the water surface without dilution, although it may be diluted to a maximum of 10% in water using a high shear injection system when spraying higher volumes of liquid is desired. Alternatively, the compound may be diluted in a petroleum distillate or a suitable fatty acid ester, such as methyl or ethyl oleate to a range of 5% to 50% and applied with conventional spray equipment. A suggested rate of application for the undiluted liquid compound includes about 0.2-1.0 gallons/acre, depending upon the habitat and condition of the water. The high end of the dosage rate is recommended when spraying habitats where multi-directional winds of 10 mph or greater are expected to persist, as the displacement of the surface film may result in poor control.

Upon application using conventional application methods, for example, spraying, the mono-molecular film spreads over standing water habitats. The film reduces the surface tension of the water rendering it difficult for mosquito larvae and pupae to attach, causing them to drown. Emerging adult mosquitoes or midges are unable to fully emerge and will drown. The film interrupts the critical air/water interface in the larval and pupal development cycle. An advantage is that mosquitoes, midges and black flies are unlikely to develop resistance to the compound because control is through a physical mode of action.

Other conventional application methods may include spreading the compound in a granular form over a selected surface area, either as pretreatment or directly to standing water. In the methods according to an aspect of the invention, mosquito populations can be effectively controlled by utilizing effective amounts of the compound, whether in liquid or granular form. The compound may be formulated into a granular form by conventional methods known in the art.

Advantageously, the compound and methods according to the invention provide ease of application in view of the spreadability properties of the surfactant. The compound is relatively non-toxic to non-target species, for example, the compound works by physical action, i.e., the surface tension of the water is affected, but not by chemical toxicity. Moreover, the compound is biodegradable.

Unless otherwise defined, all technical and scientific terms used herein have the same meaning as commonly understood by one of ordinary skill in the art to which the invention belongs. Although methods and materials similar or equivalent to those described herein can be used in the practice or testing of the invention, suitable methods and materials are described below. In addition, the materials, methods and examples are illustrative only and are not intended to be limiting.

EXAMPLES

Preparation of Ethoxylated Branched Alcohol 728 g. of NEODOL® 67 (available from Shell Chemicals of Texas) and 4.9 g of hydrotalcite (CAS 11137-98-7) available from Mitsui, for example, were charged into a stainless pressure reactor at room temperature. The reactor was sealed, degassed, and purged with nitrogen. The reactor was heated to 150° C.-160° C. 257 g of ethylene oxide was added into the reactor at a temperature of 150° C.-170° C. After the ethylene oxide addition, the reaction was continued at the reaction temperature for an additional two hours to ensure completion. The residual ethylene oxide was removed by vacuum stripping at 150° C.-160° C. for thirty minutes. The product was then washed and dried. About 935 g of product was obtained.

Biodegradation Assessment

Samples of test substances, Agnique MMF® and substances according to the invention (N-MMF) were tested to assess the degree of ready biodegradability, using a procedure outlined in Vizon SciTech Inc. (Vizon) Standard Operating Procedure (SOP), "Manometric Respirometry Test (SOP 1705), which is based on the OECD Guideline 301F for the "Manometric Respirometry Test (OECD 1992). The biodegradability was assessed by measuring the consumption of oxygen by a microbial population (activated sludge) exposed to the test substances under controlled conditions, and by expressing that oxygen uptake (corrected for uptake by inoculum blank) as a percentage of the theoretical oxygen demand (ThOD) of the test substances.

Results for the experiment showed that on Day 28, there was a 79% mean biodegradation in the bottles containing Agnique MMF® (A-MMF), and 82% mean biodegradation in the bottles containing NEODOL® 67-based MMF (N-MMF) according to an aspect of the invention. The ten-day window for both test substances began on Day 2, with A-MMF having undergone biodegradation at 17% and N-MMF at 21%, and ended on Day 12 with 63% and 71% biodegradation for A-MMF and N-MMF, respectively. For the reference substance and toxicity control groups, biodegradation was significantly higher in the toxicity controls (Containing test substance and reference substance) than in the reference substance alone. On Day 28, there was 71% biodegradation in the reference substance, 123% in the toxicity control containing A-MMF, and 135% in the toxicity control containing N-MMF. In conclusion, biodegradation for both A-MW and N-MMF reached greater than 60% within a 10-day window, and therefore both substances are considered to be readily biodegradable.

Procedures for Examples 1 and 2

Two formulations, namely, N-MMF and A-MMF, were evaluated as to effectiveness in controlling *Culex quinquefasciatus,* and *Ochlerotatus taeniorhynchus* mosquito larvae.

The tests were conducted in laboratory beakers in aluminum water baths which were approximately 5 feet long×21 inches wide×6 inches deep aluminum pans filled with approximately 4 inches of water. Each bath held up to 48 beakers. An immersion circulator (Fisher Scientific Products) maintained the water temperature at 27°±1° C. Twenty-five (25) $2^{nd}$ or $3^{rd}$ instar larvae were transferred from rearing pans (containing well water) into 50 ml of well water and transferred into 200 ml of aerated well water in 600 ml PYREX® beakers (Fisher Scientific Products). For assays on *O. taeniorhynchus* larvae, a sufficient amount of salt (sodium chloride) was added to the water to make a 3 ppt salt-water solution. Three dilutions of the test materials were formulated with reagent grade acetone (Fisher Scientific Products) and one ml of the dilutions pipetted into the respective treatment beakers. A similar number of beakers remained untreated. Application rates were 1.0 g/acre; 0.5 g/acre; and 0.25 g/acre. Assessments were made at 24, 48, and 72 hours, post-treatment.

Example 1

The larval mortality of *Ochlerotatus taeniorhynchus,* also known as black salt marsh mosquito, was determined using different concentrations of N-MMF samples (0.25 gallons per acre; 0.5 gallons per acre, and 1.0 gallon per acre), according to an aspect of the invention, and AGNIQUE® MMF. The results are illustrated below.

| | *Ochlerotatus taeniorhynchus* | | | | | | | |
|---|---|---|---|---|---|---|---|---|
| | N-MMF | | | | A-MMF | | | |
| Hrs | Control | 0.25 | 0.5 | 1.0 | Control | 0.25 | 0.5 | 1.0 |
| 24 | 0 | 21.33 | 21.33 | 40.0 | 0 | 10.67 | 13.33 | 13.33 |
| | 0 | 13.33 | 32.0 | 92.0 | 0 | 1.33 | 2.67 | 22.67 |
| | 0 | 2.67 | 21.33 | 52.0 | 0 | 8.0 | 24.0 | 44.0 |
| Ave | 0 | 12.44 | 24.89 | 61.33 | 0 | 6.67 | 13.33 | 26.67 |
| 48 | 0 | 33.33 | 49.33 | 68.0 | 0 | 20.0 | 44.0 | 57.33 |
| | 0 | 76.0 | 93.33 | 100.0 | 2.67 | 68.0 | 70.67 | 77.23 |
| | 0 | 60.0 | 76.0 | 93.33 | 0 | 77.33 | 77.33 | 92.0 |
| Ave. | 0 | 56.44 | 72.89 | 87.11 | 0.89 | 55.11 | 64.0 | 75.52 |
| 72 | 1.33 | 77.33 | 93.33 | 100.0 | 6.67 | 76.0 | 84.0 | 84.0 |
| | 1.33 | 65.33 | 82.67 | 93.33 | 2.67 | 85.33 | 84.0 | 94.67 |
| Ave. | 1.33 | 71.33 | 88.0 | 96.66 | 4.67 | 80.66 | 84.0 | 89.33 |

At 24-hours post-treatment, all concentrations of N-MMF provided improved larval mortality over A-MMF. At 48-hours post-treatment, all concentrations of N-MMF provided improved larval mortality, but the difference between the products was less (a 15-25% improvement). At 72-hours post-treatment, all concentrations of N-MMF were nearly equivalent to A-MMF in larval mortality The data supports the conclusion that the compound according to the invention kills mosquito larvae faster than A-MMF. There is a higher mortality using N-MMF at the same dose rate of A-MMF.

Example 2

The larval mortality of *Culex quinquefasciatus*, also known as the Southern house mosquito, was determined as in the above Example. The results are illustrated below.

| | *Culex quinquefasciatus* | | | | | | | |
|---|---|---|---|---|---|---|---|---|
| | N-MMF | | | | A-MMF | | | |
| Hrs | Control | 0.25 | 0.5 | 1.0 | Control | 0.25 | 0.5 | 1.0 |
| 24 | 0 | 48.0 | 62.67 | 78.67 | 0 | 28.0 | 41.33 | 73.33 |
| | 0 | 10.67 | 37.33 | 40.0 | 0 | 57.33 | 50.67 | 89.33 |
| | 0 | 50.67 | 37.33 | 54.67 | 0 | 0 | 13.33 | 44.0 |
| Ave | 0 | 36.45 | 45.78 | 57.78 | 0 | 28.44 | 35.11 | 68.89 |
| 48 | 0 | 65.33 | 85.33 | 85.33 | 5.33 | 36.0 | 50.67 | 74.67 |
| | 1.33 | 33.33 | 62.67 | 74.67 | 4.0 | 74.67 | 73.33 | 96.0 |
| | 0 | 81.33 | 85.33 | 90.67 | 0 | 38.67 | 57.33 | 88.0 |
| | 0 | 85.33 | 86.67 | 97.33 | 0 | 21.33 | 41.33 | 81.33 |
| Ave. | 0.33 | 66.33 | 80.0 | 87.0 | 2.33 | 42.67 | 55.66 | 85.0 |
| 72 | 0 | 90.67 | 88.0 | 90.67 | 0 | 61.33 | 78.67 | 92.0 |
| | 0 | 85.33 | 86.67 | 97.33 | 0 | 36.0 | 56.0 | 86.67 |
| Ave. | 0 | 88.0 | 87.33 | 94.0 | 0 | 48.66 | 67.33 | 89.33 |

The data indicates that N-MMF is a more effective larvacide than A-MMF, even at lower doses. At 0.25 gallon/acre and 0.5 gallon/acre, the N-MMF product provided an increased larval mortality of between 26-80% from 24 to 72 hours. Also, only 0.25 gallon/acre of N-MMF were needed to provide for an 88 percent (88%) of larval mortality that required 1.0 gallon/acre of A-MMF. It was also observed that the initial or early mortality with N-MMF was greater than the corresponding dose of A-MMF.

The invention has been described with reference to specific embodiments. One of ordinary skill in the art, however, appreciates that various modifications and changes can be made without departing from the scope of the invention as set forth in the claims. For example, although the Examples use certain linear and branched alcohols, other alcohols may be suitable for arriving at the compounds according to the invention. Accordingly, the specification is to be regarded in an illustrative manner, rather than a restrictive view and all such modifications are intended to be included within the scope of the invention.

Benefits, other advantages, and solutions to problems have been described above with regard to specific embodiments. The benefits, advantages, solutions to problems and any element(s) that may cause any benefit, advantage, or solution to occur or become more pronounced are not to be construed as a critical, required, or essential feature or element of any or all of the claims.

What is claimed is:

1. A method for controlling the aquatic stages of aquatic breeding insects, comprising the step of treating a body of water with a compound in an amount effective to control at least one aquatic stage of an aquatic breeding insect, said compound comprising an ethoxylated C10-C24 alcohol having about 2 to about 4 moles of ethylene oxide per mole of alcohol, wherein the carbon chain is linear or branched, and wherein said ethoxylated alcohol is water-insoluble and forms a film on the surface of said body of water.

2. A method for controlling the aquatic stages of aquatic breeding insects, comprising applying a compound in an amount effective to control at least one aquatic stage of an aquatic breeding insect, to a selected surface during the larval, pupal, or adult stages of aquatic breeding insects, said compound comprising an ethoxylated C10-C24 alcohol having about 2 to about 4 moles of ethylene oxide per mole of alcohol, wherein the carbon chain is linear or branched, and wherein said ethoxylated alcohol is water-insoluble and forms a film on the surface of a body of water.

3. The method of claim 1, wherein said alcohol comprises a C12-C17 alcohol or mixture of such alcohols.

4. The method of claim 3, wherein said alcohol comprises a C16-C17 alcohol or mixture of such alcohols.

5. The method of claim 4, wherein said alcohol comprises a C16-C17 mono-branched primary alcohol or mixture of such alcohols.

6. The method of claim 3, wherein said alcohol comprises a C15 alcohol.

7. The method of claim 1, wherein said aquatic breeding insects comprise mosquitoes, midges, or black flies.

8. The method of claim 1, wherein said branched alcohol contains an alkyl group comprising about 1 to about 5 carbon atoms.

9. The method of claim 8, wherein said alkyl group is methyl.

10. The method of claim 8, wherein said alkyl group is selected from the group consisting of ethyl, propyl, isopropyl, butyl, isobutyl, and pentyl.

11. The method of claim 1, wherein said compound is applied in a liquid, gel, encapsulated liquid or granular formulation.

12. The method of claim 2, wherein said alcohol comprises a C12-C17 alcohol or mixture of such alcohols.

13. The method of claim 12, wherein said alcohol comprises a C16-C17 alcohol or mixture of such alcohols.

14. The method of claim 13, wherein said alcohol comprises a C16-C17 mono-branched primary alcohol or mixture of such alcohols.

15. The method of claim 12, wherein said alcohol comprises a C15 alcohol.

16. The method of claim 2, wherein said aquatic breeding insects comprise mosquitoes, midges, or black flies.

17. The method of claim 2, wherein said branched alcohol contains an alkyl group comprising about 1 to about 5 carbon atoms.

18. The method of claim 17, wherein said alkyl group is methyl.

19. The method of claim 17, wherein said alkyl group is selected from the group consisting of ethyl, propyl, isopropyl, butyl, isobutyl, and pentyl.

20. The method of claim 2, wherein said compound is applied in a liquid, gel, encapsulated liquid or granular formulation.

21. A composition for controlling the aquatic stages of aquatic breeding insects, comprising:
   (a) about 5% to about 50% of at least one ethoxylated C10-C24 alcohol having about 2 to about 4 moles of ethylene oxide per mole of alcohol, wherein the carbon chain is linear or branched; and
   (b) a solvent selected from the group consisting of petroleum distillates, fatty acid esters, and mixtures thereof, wherein said ethoxylated alcohol is water-insoluble and forms a film on the surface of a body of water, and is effective at controlling at least one aquatic stage of an aquatic breeding insect.

22. The composition of claim 21, wherein said solvent (b) comprises methyl oleate or ethyl oleate.

* * * * *